United States Patent [19]
Chaudhuri et al.

[11] Patent Number: 5,922,310
[45] Date of Patent: Jul. 13, 1999

[54] COMPOSITIONS FOR PREVENTING THE FADING OF ARTIFICIAL HAIR DYE

[75] Inventors: Ratan K. Chaudhuri, Lincoln Park, N.J.; Janusz Jachowicz, Bethel, Conn.; Bruce C. Locke, Easton, Pa.

[73] Assignee: ISP Investments Inc., Wilmington, Del.

[21] Appl. No.: 09/040,650

[22] Filed: Mar. 17, 1998

[51] Int. Cl.[6] .................................................. B29D 31/00
[52] U.S. Cl. .................................. 424/70; 424/71; 424/72
[58] Field of Search .................................. 424/70, 71, 72

[56] References Cited

U.S. PATENT DOCUMENTS 4,009,255  2/1977  Kalopissis et al. ........................ 424/70
4,695,653  9/1987  Kalopissis et al. ...................... 564/505

*Primary Examiner*—Terressa Mosley
*Attorney, Agent, or Firm*—William J. Davis; Walter Katz; Marilyn J. Maue

[57] ABSTRACT

A composition for preventing the fading of artificial hair dye and/or slowing down the oxidation of hair includes a cationic antioxidant phenol in an amount of about 0.01–1% wt/wt.

9 Claims, No Drawings

COMPOSITIONS FOR PREVENTING THE FADING OF ARTIFICIAL HAIR DYE

BACKGROUND OF THE INVENTION

1. Field of the Invention

This invention relates to compositions for preventing the fading of artificial hair dye and/or slowing down the oxidation of hair, and more particularly, to a cationic phenol antioxidant for achieving this result effectively.

2. Description of the Prior Art

Hair comprises predominantly certain polypeptide chains that are held together by disulfide bonds that link adjacent polypeptide chains. These bonds are formed from two cysteine amino acid residues on the adjacent keratin polypeptides. The disulfide bonds impart its mechanical strength and extensibility to the hair. However, exposure to sun tends to cause these disulfide bonds to break, predominantly on the outer surface of the hair and the outer surface of the hair cuticle. This effect makes the hair stiff and brittle in dry weather and frizzy in humid weather. The hair also loses its color and luster.

Photofilters or UV-absorbers have been employed in cosmetic products for many years to protect coloring dyes from photofading. Recently, sunscreens also have been added to hair care products to guard against the deleterious effects of solar irradiation on the hair.

Photoprotection of melanin in skin has been intensively investigated over the last years. For hair protection, several approaches have been described, such as the deposition of photofilters on the hair surface, and the use of antioxidants, or free radical scavengers. See W. P. Smith and F. J. Penna, U.S. Pat. No. 4,786,493.

Accordingly, it is an object of the present invention to provide new and improved compositions for preventing the fading of artificial hair dye on the hair of the user and/or slowing down the oxidation of hair.

SUMMARY AND DESCRIPTION OF THE INVENTION

What is described herein is a composition for preventing the fading of artificial hair dye and/or slowing down the oxidation of hair. The composition includes one or more of the following cationic antioxidants:

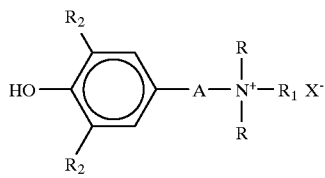

where

A is $(CH_2)_n$, $(CH_2)_n CONH(CH_2)_m$, $(CH_2)_n COO(CH_2)_m$, $CONH(CH_2)_n$, $COO(CH_2)_n$;

n is an integer from 1–12, preferably 1–6;

m is an integer from 1–12, preferably 1–6;

R is $C_1$ to $C_6$ alkyl, linear or branched;

$R_1$ is $C_1$ to $C_{30}$ alkyl, linear or branched;

$R_2$ is OH, $C_1$ to $C_6$ alkyl, linear or branched or $O(C_1$ to $C_6$ alkyl), linear or branched.

X is an anion e.g. halide, methosulfate, tosylate or mesylate. In preferred embodiments, $R_2$ is $C(CH_3)_3$, $CH(CH_3)_2$, OH, $OCH_3$ or $OC_2H_5$.

A preferred antioxidant is 2,6-di-tertbutyl-α-dimethylamino-p-cresol, preferably in the form of a quat of the compound, such as the dodecyl tosylate quat.

Preferably the composition of the invention includes the antioxidant compound in an amount of about 0.01–1% wt/wt.

Most preferably, the composition is a leave-on or rinse-off solution.

The compositions of the invention also can be used for skin treatment to slow down oxidation of skin lipids and proteins, or to prevent oxidation of cosmetic ingredients in cosmetic formulations.

The invention will now be illustrated by the following examples.

EXAMPLE 1

Dodecyl Tosylate Quat. of 2.6-Di-tertbutyl-α-Dimethylamino-p-Cresol

To 50 g of 2,6-di-tertbutyl-α-dimethylamino-p-cresol dissolved in 250 ml of isopropanol (IPA) was added 65.9 g of dodecyl tosylate, agitated and gradually heated to 110° C. to remove IPA. The reaction mixture then was maintained at 110° C. for 2 hours before 30 mm Hg vacuum is applied for 30 minutes. The residue was recrystallized from methyl ethyl ketone, washed and dried to give a white solid in 90% yield.

EXAMPLE 2

1% of 2,6-di-tertbutyl-α-dimethylamino-p-cresol

60% absolute EtOH.

39% deionized water.

Two test solutions were used. The first was as described above; the second was neutralized to pH~7 with a 20% citric acid solution.

A sample of 65% gray hair dyed with Clairol Nice'N Easy Auburn 112 showed a total color change of 5.51±0.29 after 40 hours irradiation. Samples treated with the 1% and 1% neutralized solutions of the compound showed total color changes of 6.10±0.42 and 3.20±0.71, respectively, after 40 hours irradiation. The neutralized compound gave much better color protection than the unneutralized compound.

EXAMPLE 3

1% of the compound of Example 1

60% absolute EtOH;

39% deionized water.

A sample of 65% gray hair dyed with Clairol Nice'N Easy Auburn 112 showed a total color change of 5.51±0.29 after 40 hours irradiation. A sample treated with the 1% solution of the compound showed a total color change of only 3.57÷0.90 after 40 hours irradiation.

The cationic antioxidant compounds of the invention are particularly useful because they are substantive to hair; i.e. they can treat the hair and be rinsed thereafter with water while remaining intact on the hair. Such compositions also can be formulated with surfactants while preserving the substantive character of the antioxidant.

The compositions of the invention can also be used for skin treatment; i.e. to slow down oxidation of skin lipids and proteins; and, in general, to prevent oxidation of cosmetic components, in cosmetic formulations.

While the invention has been described with particular reference to certain embodiments thereof, it will be understood that changes and modifications may be made which are within the skill of the art. Accordingly, it is intended to be bound only by the following claims.

What is claimed is:

1. A composition for preventing the fading of artificial hair dye and/or slowing down the oxidation of hair which includes one or more of the following cationic antioxidants:

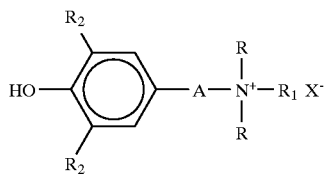

$A = (CH_2)_n$, $(CH_2)_n CONH(CH_2)_m$, $(CH_2)_n COO(CH_2)_m$, $CONH(CH_2)_n$, $COO(CH_2)_n$;

$n = 1-12$;

$m = 1-12$;

$R = C_1$ to $C_6$ alkyl;

$R_1 = C_1$ to $C_{30}$ alkyl;

$R_2 = OH$, $C_1$ to $C_6$ alkyl, $O(C_1$ to $C_6$ alkyl); and $X = $ an anion.

2. A composition according to claim 1 which is a solution.

3. A composition according to claim 1 which includes a cationic antioxidant which is a quat of 2,6-di-tert-butyl-α-dimethylamino-p-cresol.

4. A composition according to claim 1 wherein the compound is present in an amount of about 0.01–1% wt/wt.

5. A composition according to claim 1 which is a leave-on or rinse-off formulation.

6. A composition to slow down oxidation of skin lipids and proteins or to preserve components in a cosmetic formulation which includes the cationic antioxidant of claim 1.

7. An antioxidant which is 2,6-di-tert-butyl-α-dimethylamino-p-cresol.

8. A cationic antioxidant which is a quat of the compound of claim 7.

9. A cationic antioxidant according to claim 8 which is the dodecyl tosylate quat.

* * * * *